United States Patent [19]

Schmid

[11] Patent Number: 4,480,638
[45] Date of Patent: Nov. 6, 1984

[54] CUSHION FOR HOLDING AN ELEMENT OF GRAFTED SKIN

[76] Inventor: Eduard Schmid, Böheimstrasse 37, D7000 Stuttgart 1, Fed. Rep. of Germany

[21] Appl. No.: 321,169

[22] PCT Filed: Mar. 11, 1980

[86] PCT No.: PCT/DE80/00025

§ 371 Date: Nov. 9, 1981

§ 102(e) Date: Nov. 9, 1981

[87] PCT Pub. No.: WO81/02516

PCT Pub. Date: Sep. 17, 1981

[51] Int. Cl.³ ............................................. A61F 13/00
[52] U.S. Cl. ..................................... 128/155; 128/118; 604/23; 604/305; 604/385
[58] Field of Search .................... 128/95, 96, 112, 117, 128/118, 157, 155, 156, 163, 165, 158; 604/289, 290, 304, 305, 385, 23–25

[56] References Cited

U.S. PATENT DOCUMENTS

| | | | |
|---|---|---|---|
| 397,545 | 2/1889 | Greeno | 128/118 |
| 404,307 | 5/1889 | Rorick | 128/118 |
| 413,152 | 10/1889 | Streeter et al. | 128/118 |
| 449,473 | 3/1891 | Garcia | 128/118 |
| 948,306 | 2/1910 | Bunker | 128/118 |
| 1,379,660 | 5/1921 | Taylor | 604/305 |
| 1,892,804 | 1/1933 | Pease | 128/117 |
| 1,925,615 | 9/1933 | Stuart | 128/112 |
| 2,070,727 | 2/1937 | Hamann | 128/117 |
| 3,171,410 | 3/1965 | Towle, Jr. et al. | 128/155 |
| 3,616,156 | 10/1971 | Scholl | 128/155 |
| 3,687,136 | 8/1972 | Carmody | 128/156 |
| 3,874,387 | 4/1975 | Barbieri | 128/155 |
| 3,885,559 | 5/1975 | Economou | 128/156 |
| 3,903,882 | 9/1975 | Augurt | 128/155 |
| 3,952,735 | 4/1976 | Wirtschafter et al. | 128/163 |
| 4,181,127 | 1/1980 | Linsky et al. | 128/155 |
| 4,202,331 | 5/1980 | Yale | 128/155 |
| 4,224,941 | 9/1980 | Stivala | 604/23 |
| 4,224,945 | 9/1980 | Cohen | 128/155 |
| 4,231,357 | 11/1980 | Hessner | 128/156 |
| 4,257,412 | 3/1981 | Guttentag | 128/112 |
| 4,275,718 | 6/1981 | Jungmann | 128/95 |
| 4,303,063 | 12/1981 | Stahl | 128/163 |
| 4,436,089 | 3/1984 | Schmid | 128/155 |

FOREIGN PATENT DOCUMENTS

| | | | |
|---|---|---|---|
| 1491207 | 4/1969 | Fed. Rep. of Germany . | |
| 627900 | 10/1927 | France | 128/118 |
| 2252839 | 6/1975 | France . | |
| 2382900 | 10/1978 | France . | |
| 115185 | 5/1918 | United Kingdom . | |
| 910340 | 6/1946 | United Kingdom . | |
| 641061 | 8/1947 | United Kingdom . | |

Primary Examiner—Richard J. Apley
Assistant Examiner—Harry J. Macey
Attorney, Agent, or Firm—Burmeister, York, Palmatier, Hamby & Jones

[57] ABSTRACT

A cushion for pressing an element of grafted skin against the body surface, wherein the portion (2) to be applied to the body has a window or opening (4) the dimensions of which approximately equal that of the graft. The edges (6) of the window (4) are attached to the skin so as to be impervious to air or liquids. The filling medium of the cushion (air or a liquid) is maintained under pressure.

4 Claims, 4 Drawing Figures

CUSHION FOR HOLDING AN ELEMENT OF GRAFTED SKIN

FIELD OF THE INVENTION

The present invention relates to a cushion for pressing skin grafts to the surface of the human body.

BACKGROUND OF THE INVENTION

In the surgical grafting of skin portions, especially when a full-thickness skin transplantation is performed, it is of critical importance that uniform pressure be applied to the graft over the entire area thereof to press the transplanted skin firmly against the respective surface area of the human body. Such evenly applied pressure must be maintained from six to eight days, with slight individual variations being permissible. It is known to use for this purpose a pressure dressing which includes a cushion which is larger than the section of the grafted skin so that the graft over its entire surface area is evenly pressed against the lesion. (Ferris Smith: Plastic and Reconstruction Surgery, W. B. Saunders Co., 1950, pages 26 and 27.)

This procedure, however, has certain disadvantages. Since the familiar cushions are made of rubber, the accumulation of albumin secretions between the cushion and the surface of the graft is encouraged, and the cushion prevents air from reaching the surface of the graft. Moreover, even with the most scrupulous care it is not always possible to protect the surface area of the cushion in contact with the grafted skin from the effects of the pressure exerted by the bandage, resulting in the formation of folds in the cushion, especially when the skin portion is grafted onto a strongly curved body part. Such folds in the cushion cause corresponding impressions or similar folds on the transplanted skin which remain visible even after complete healing.

SUMMARY OF THE INVENTION

It is the object of the present invention to overcome the foregoing disadvantages and to provide a pressure dressing for use with skin grafts. This is accomplished according to the invention in that the cushion is provided with a cutout or window on the side facing the body, and that the window is at least approximately as large as the grafted skin section.

In applying the pressure dressing, the cushion is placed in such a manner that its aperture or window comes to lie over the skin graft. The edge of the window is adhesively fastened to the skin. It may additionally be stitched onto the skin and the points of stitching may further be sealed off with an adhesive or the like if the stitches are located in the region of the window edge so as to ensure a complete sealing thereof.

The cutout or window is of the same general shape as the skin graft. Some embodiments of the invention provide for the cutout to be somewhat smaller than the skin graft so that the edge of the cutout or window is disposed on the skin graft. Alternatively, the window may be slightly larger than the skin graft in which case the window edge is disposed on the heathly skin. The graft may in conventional fashion be sutured along the edge of the wound. However, suturing is not required if, according to the first embodiment of the invention, the edge of the window is adhesively attached not only to the edge of the skin graft, but also to the surrounding healthy skin.

The benefits of the cushion according to the invention are, first, that the area of the skin outlined by the open window will not perspire, and the secretion of albumin and other substances is either prevented or will not lead to skin irritations, because the area of the skin graft is ventilated through the window. Furthermore, it is possible to supply the grafted skin through the window with oxygen or a nutrient solution, to promote or appropriatedly direct the healing process. Finally, it will be appreciated that there will be no fold formation in the cutout area of the cushion, namely, over the grafted skin, so that this disadvantage of the prior art cushion is eliminated. If the side of the cushion opposite the open communication afforded by the window, i.e. facing away from the body surface is made of a transparent material, the window will permit a visual observation of the healing process, i.e. the degree of blood circulation in the grafted skin section. If necessary, corrective action may be taken by introducing an appropriate treatment agent into the cushion. For this reason, one embodiment of the invention provides for the side of the cushion opposite the window to be made of a transparent material, such as a suitable plastic, or the like.

The window in the cushion may be cut out in the shape of the skin graft immediately before applying the pressure dressing. For the healing process to proceed, however, it is not required that the window edge exactly coincide with the edge of the grafted skin section. Rather, the edge of the window in the cushion may extend both partly over the grafted skin and partly over the healthy skin. The window may also be considerably larger than the transplanted skin section without adversely affecting the healing process. Thus, cushions having windows of various dimensions may be made in advance and kept in storage for ready use by the surgeon. In such cases, the edge of the window may be provided with an adhesive to attach the cushion to the skin or the skin graft, respectively.

Some of the emobodiments of the invention provide for a valve on the cushion for adjusting the pressure inside the cushion. Connected to the valve may be devices, known per se, for producing, controlling and/or maintaining the pressure in the cushion.

One emobodiment of the cushion according to the invention is provided on the side opposite the side in contact with the body with a rigid plate which may be transparent to accommodate the embodiment described in the foregoing. The plate may conform to the contour of the part of the human body to which the cushion is applied. This embodiment of the invention has the advantage that any danger of fold formation in portions of the cushion is substantially reduced.

The cushion according to the invention may be pressed against the body surface by means of an elastic bandage, whereby the rigid plate may or may not be included. For tightly holding the cushion to the extremities, an elastic hose has proven useful.

Another embodiment of the invention is provided not only with one valve to generate, maintain or control the pressure inside the cushion and/or to fill the cushion with a liquid, but features two valves to permit the air and a liquid to be exchanged in the cushion without affecting the pressure in the cushion to any appreciable extent. By introducing air through one valve passage, a liquid contained in the cushion may be forced out through the other passage and, conversely, air in the cushion may be vented through the other opening. The two valve openings may also be used continuously to renew the fluid or air under pressure in the cushion or to have the air or fluid circulate through a medium for effecting special treatment of such air or liquid as, for example, withdraw moisture from the air to prevent perspiration or wound water from collecting in the cushion. It is obvious that fluid may also be suctioned off through one of the valves.

In yet another embodiment of the invention, the cushion contains an agent which binds moisture and hence dries the air in the cushion. Such a dehumidifier may be kept separate from the hollow interior of the cushion by a semipermeable partition made, for example, of a suitable plastic material. The partition will allow moisture to permeate only in the direction of the dehumidifying agent.

The drawings illustrate several embodiments of the invention, in which:

DETAILED DESCRIPTION OF ILLUSTRATIVE EMBODIMENTS

Figure 1:
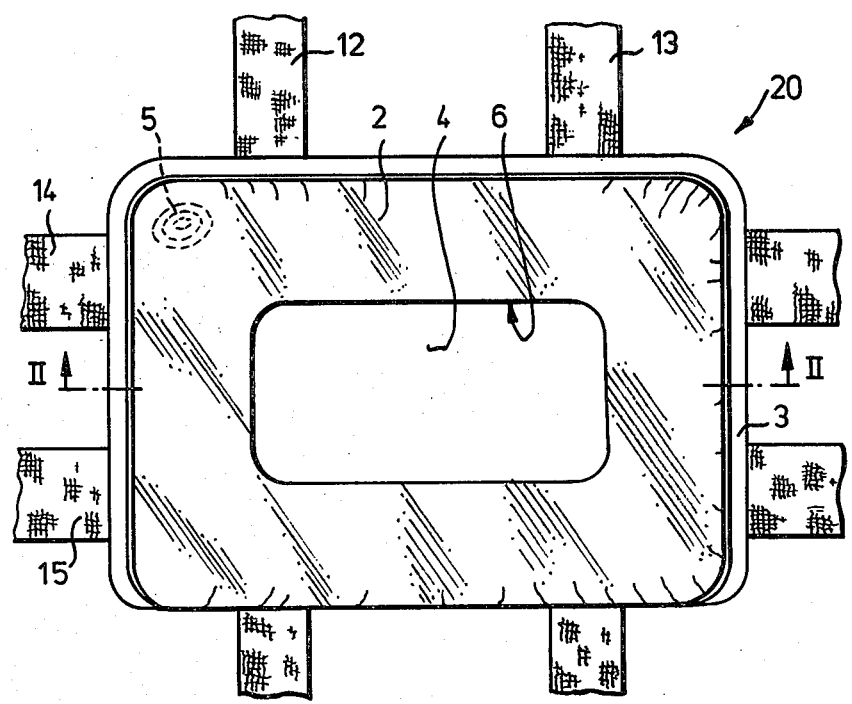
FIG. 1 is a top plan view of the side of the cushion, accord-to one embodiment of the invention, which is applied to the part of the human body requiring treatment.
Figure 2:
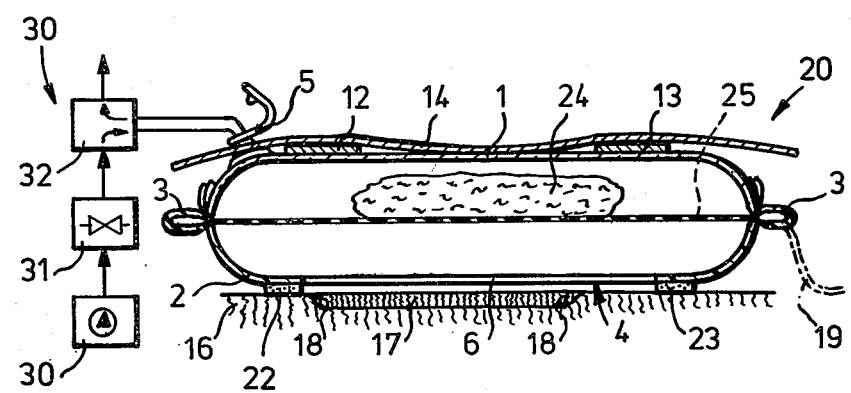
FIG. 2 is a sectional view of the cushion of FIG. 1 taken along the line II—II.

In the embodiment illustrated in FIGS. 1 and 2, a pillow-shaped cushion 2D is comprised of two sheets or foils 1 and 2 of latex rubber or some other suitable resilient plastic material. The sheets or side walls 1 and 2 are joined at their edges by a seam 3. The side wall 2 of the cushion 2D which is in contact with the body surface 16 as the pressure dressing or bandage 12, 13, 14, 15 is applied, is provided with a cutout, window or opening 4. Close to the edge of the cushion 2D, the sheet 1 has welded therein a valve 5. The window 4 is larger than the element 17 of grafted skin so that the edge or marginal portion 6 directed toward and surrounding the window in this embodiment of the invention is adhesively attached to the body surface 16, as by means of adhesive 22, 23 completely outside the range of the suture by which the skin graft 17 is attached to the body surface 16. The valve 5 is so constructed that conventional means for producing 31, maintaining 32 and controlling 33 the pressure inside the cushion 20 may readily be connected thereto. The foil or outer side wall 1 is transparent to permit observation of the skin graft 17 through the transparent foil 1 and the window open 4 without requiring removal of the dressing or bandage 12, 13, 14, 15. It will be understood that the part of the dressing 12, 13, 14, 15 arranged above the cushion 20 may also be provided with a window or opening to permit such visual observation, or that this portion of the dressing 12, 13, 14, 15 may likewise be transparent.

Figure 3:
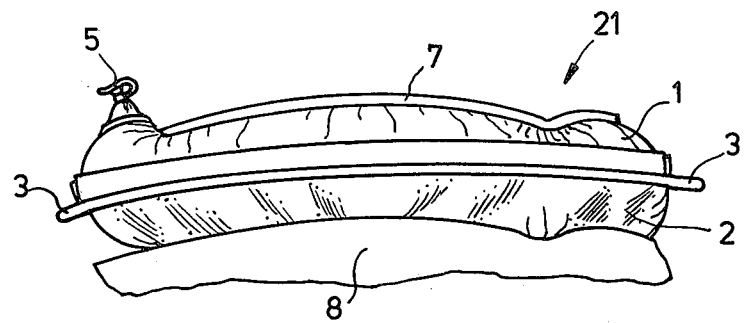
FIG. 3 is a side view of a different embodiment of the invention.

The embodiment of the invention illustrated in FIG. 3 is distinguished from the embodiment of FIGS. 1 and 2 by a rigid plate 7 which is welded, adhesively attached or in some other manner fixed in position to a cushion 21. This plate 7 conforms to the contours of the surface area of the body part 8 being covered and may likewise be transparent to facilitate a visual inspection of the grafted skin. The degree of rigidity and the size of the plate 7 are so selected as to enable the plate to distribute the pressure exerted by it evenly over the entire surface of the cushion 21 to prevent the formation of folds in the region of the sheet 2 at the underside of the cushion 21.

The valve 5 is so constructed that it may also serve as a passage for the introduction of a treatment agent into the cushion 21, while maintaining the adjusted pressure in the cushion 21, if possible. It is also feasible to provide an additional valve on the cushion 21 for this purpose.

Figure 4:
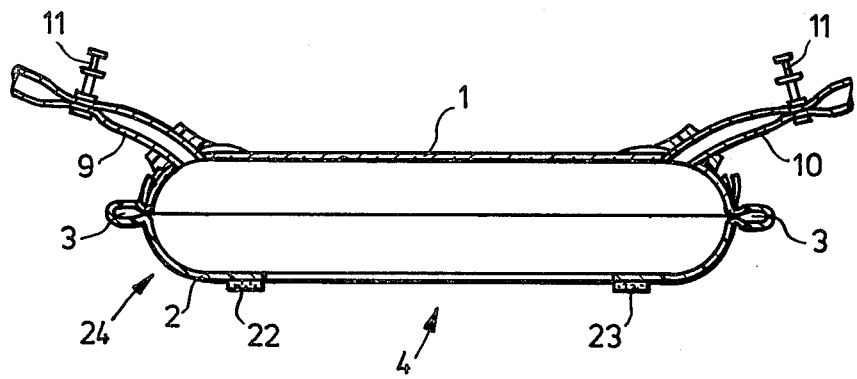
FIG. 4 is a sectional view, similar to FIG. 2, of a third embodiment of the invention.

FIG. 4 shows an embodiment comprising a cushion 24 which has two supply lines 9 and 10 leading to the interior of the cushion 24. These two lines or tubes may be fitted with devices of any kind by which the medium contained in the cushion 24 may be replaced without causing a drop in pressure, may be cleansed, or may be maintained at the desired adjustable pressure. Merely by way of demonstration, FIG. 4 shows extremely straight forward regulating means 11 on the tubes 9 and 10 which may obviously be replaced by more suitable means as the actual practice may require.

Regardless of the size of the window in the embodiment of the cushion 21 illustrated in FIG. 1, the dimensions of the window 4 may be such that its edge 6 may extend over both part of the healthy skin and part of the grafted skin, or it may extend solely over the grafted skin.

The cushion 20, 21, 24 may be pressed against the skin graft 17 with the aid of a bandage 12, 13, 14, 15 or an elastic hose. Also, either of the two sheets 1 and 2, notably the bottom sheet 2, may be made substantially larger than the other sheet so that it extends beyond the seam 3 to be used to secure the cushion 20, 21, 24 in place.

The cushion 20 in FIG. 1 may also contain any known or suitable moisture binding agent 24' which is preferably separated by any known or suitable semipermeable partition 25 from the interior of the cushion 20 which is in open communication with the skin graft 17 through the opening 4.

I claim:

1. A device for covering and applying pressure to a skin graft of a known size and shape and applied to a human body with normal skin surrounding the skin graft, said device comprising a hollow inflatable generally pillow-shaped cushion having a first side wall made of a thin flexible sheet foil material for facing and engaging the human body, said cushion having a second side wall made of a thin flexible sheet foil material and opposite from said first side wall for facing away from the human body, said first and second side walls having joined peripheral portions and forming an interior space within said inflatable cushion, said cushion and said first side wall thereof having an overall size and shape which is relatively substantially greater than the size and shape of the skin graft for overlying and protecting the skin graft and a portion of the surrounding skin, said first side wall having an open cutout window therein having a size and shape relatively corresponding generally with the size and shape of the skin graft for producing open communication through said window between the skin graft and the interior space within said cushion, the interior space within said inflatable cushion being in open communication with said skin graft through said open cutout window when said cushion is in its position of use, said first side wall having a marginal portion surrounding said open cutout window and directed toward said window for engaging the surrounding skin around the entire skin graft, first means for producing fluid-tight attachment of said marginal portion of said first side wall to the surrounding skin around the entire skin graft, and second means for producing, maintaining and controlling fluid pressure within said cushion for inflating said cushion and exerting fluid pressure against the skin graft, said marginal portion also being subject to the fluid pressure and being pressed against the surrounding skin by the fluid pressure when the cushion is in its position of use, said cushion including a semipermeable partition within said cushion and dividing the interior space within said cushion into first and second compartments on opposite sides of said semipermeable partition, said first compartment being in direct open communication with the skin graft through said open cutout window, said second compartment being separated from said first compartment by said semipermeable partition whereby the only communication between the skin graft and said second compartment is through said first compartment and said semipermeable partition, said cushion including a moisture binding agent contained within said second compartment for absorbing moisture evolved from the skin graft, said semipermeable partition being permeable by moisture while preventing direct contact between said moisture binding agent and said skin graft.

2. A device according to claim 1,
said semipermeable partition being made of a thin semipermeable plastic sheet material,
said first and second side walls being made of a thin flexible transparent plastic materials.

3. A device according to claim 1,
said second means including inlet and outlet valves connecting with said second compartment of the interior space within said cushion for circulating pressurized fluid through said second compartment.

4. A device according to claim 1,
said first means comprising adhesive material on said marginal portion of said first side wall and surrounding said open cutout window for causing said marginal portion to adhere to the skin surrounding the skin graft.

* * * * *